United States Patent [19]

Babson

[11] 4,152,269

[45] May 1, 1979

[54] COLLECTION AND SEPARATION DEVICE

[75] Inventor: Arthur L. Babson, Chester, N.J.

[73] Assignee: Warner-Lambert Company, Morris Plains, N.J.

[21] Appl. No.: 764,505

[22] Filed: Feb. 1, 1977

[51] Int. Cl.² ............... B01D 21/26; A61B 10/00
[52] U.S. Cl. ................... 210/516; 128/764; 206/219; 206/222; 210/DIG. 23; 215/247; 215/DIG. 8
[58] Field of Search ............ 128/2 F, DIG. 5; 210/83, 516, DIG. 23, DIG. 24; 215/247, 364, DIG. 8; 206/219, 222

[56] References Cited

U.S. PATENT DOCUMENTS

| | | | |
|---|---|---|---|
| 2,115,035 | 4/1938 | Morgan | 215/364 X |
| 2,631,521 | 3/1953 | Atkins, Jr. | 215/DIG. 8 |
| 2,911,123 | 11/1959 | Saccomanno | 215/247 |
| 3,696,919 | 10/1972 | Miles | 215/DIG. 8 |
| 3,761,408 | 9/1973 | Lee | 210/DIG. 24 |
| 3,780,935 | 12/1973 | Lukacs et al. | 210/DIG. 23 |
| 3,920,557 | 11/1975 | Ayres | 210/516 |
| 3,957,653 | 5/1976 | Blecher | 210/DIG. 23 |
| 3,976,579 | 8/1976 | Bennett | 210/DIG. 23 |

*Primary Examiner*—Kyle L. Howell
*Attorney, Agent, or Firm*—Albert H. Graddis; Frank S. Chow

[57] ABSTRACT

A blood collection assembly and closure therefor, for the collection, separation, isolation and storage of serum from blood. The closure is constructed of a cannula penetrable self-sealing elastomer and includes a thixotropic barrier material in a hollow central portion of the closure, so that the barrier material is sealed within the closure until blood has been collected in the collection container and centrifuged. Centrifugation forces the barrier material into a collecton container through the passageway created by the cannula.

2 Claims, 5 Drawing Figures

COLLECTION AND SEPARATION DEVICE

This invention relates to serum separators using thixotropic barriers such as disclosed in the U.S. Pat. No. 3,780,935, the disclosure of which is incorporated herein.

More particularly, this invention relates to a device for a collection separation and isolation of the serum or plasma components from whole blood without exposure of the components to contamination by the atmosphere. Generally, this device comprises an air evacuated blood collection container and a self sealing, airtight elastomeric closure for the container which is penetratable by a blood bearing cannula and which contains a sterile thixotropic material as disclosed in U.S. Pat. No. 3,780,935.

An advantage of enclosing the thixotropic material in a sealed closure is that the closure may be removed or handled without danger of contaminating the thixotropic sealant. Furthermore, when the container for the sealant is not a complete enclosure, such as in U.S. Pat. Nos. 3,780,935 and 3,976,579, there is a tendency for the loose thixotrope to coat the inner walls of the collection tube and thus inhibit surface activation of blood coagulation.

Other objectives and advantages will become apparent from the detailed description which is to be taken in conjunction with the drawings in which.

Figure 1:
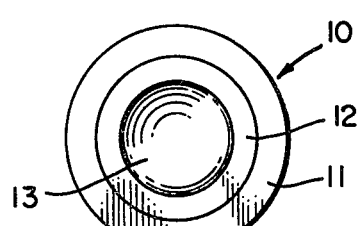
FIG. 1 is a top plan view of an enclosure according to my invention.

More particularly, my invention is that of a novel self-sealing elastomeric closure 10 consisting of a hollow cylindrical body 24 having an opened upper end defined by circumferential surface 11 and a closed lower end of reduced thickness to provide a thin, cannula penetrable zone; the axially extending hollow shaft portion of the body 24 defining a reservoir 21 for holding a sterile thixotropic sealant barrier material; the opened upper end is closed by a self-sealing elastomeric seal 12 having a central portion 13 of reduced thickness to provide a thin cannula penetrable zone.

The upper portion of tubular body 24 is surmounted by a coaxial head 23 of greater diameter and having a flange member 34 adapted to overlie with fluid secureness the open end of a sample collection container 33.

The circular opening defined by surface 11 comprises an inner shaft portion 25 having an inwardly extending shoulder 22. After filling cavity 21 with a sterile thixotrope, seal 12 is fitted into the opening and lies on shoulder 22 and against inner shaft 25 with sufficient contact to produce an airtight and fluid tight seal.

The filled closure is then seated upon flange member 34 in the open end of an evacuated collection container 33 of the Vacutainer (trademark) type and is held in intimate contact within the inner walls of the container by a vacuum seal 31 to hermetically seal the open end of the container 33.

Figure 3:
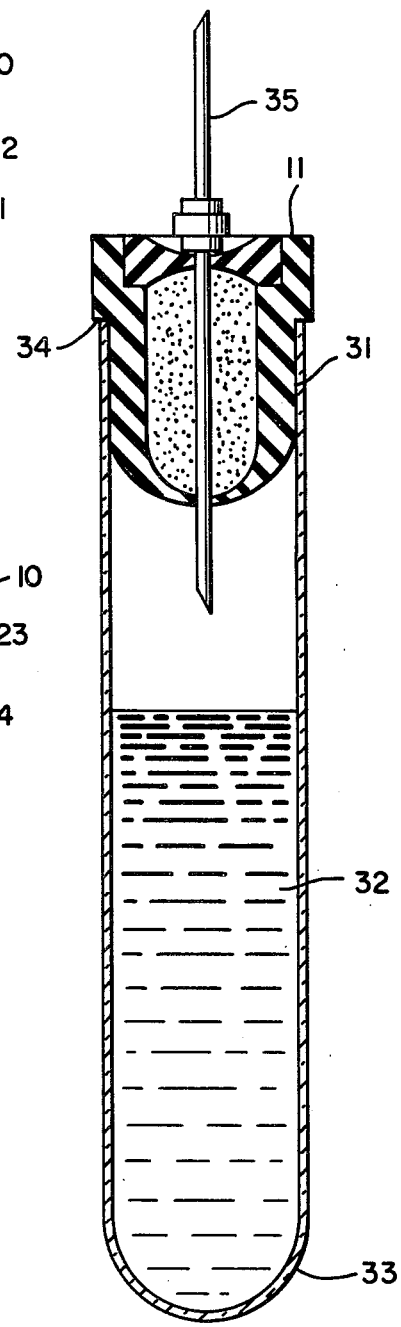
FIG. 3 is a longitudinal cross-sectional view of the collection device according to this invention.

The operation of the assembly may be readily appreciated by referring to the cross-sectional side elevation of FIG. 3. Generally the assembly is at least partially air evacuated so that there is a partial negative pressure within the container 33. As seen in FIG. 3, a blood bearing cannula 35 has been inserted through the cannula zone 13 of the closure seal, through the thixotrope containing reservoir 21, and on through the cannula penetrable zone of the lower end of the closure. Cannula 35 is connected to a blood transfer apparatus conventionally employed to transfer blood 32 from the patient into the collection container.

Upon completion of collecting blood 32 in container 33, the cannula 35 is withdrawn from the assembly leaving a lower passageway 44 through the closed lower end of closure 10 and an upper passageway 45 through the central portion 13 of seal 12. Because of the self-sealing characteristic of closure 10 and seal 12, passageway 44 and 45 will immediately self-seal upon withdrawing cannula 35 from the assembly thereby retaining the thixotrope within reservoir 21.

Figure 4:
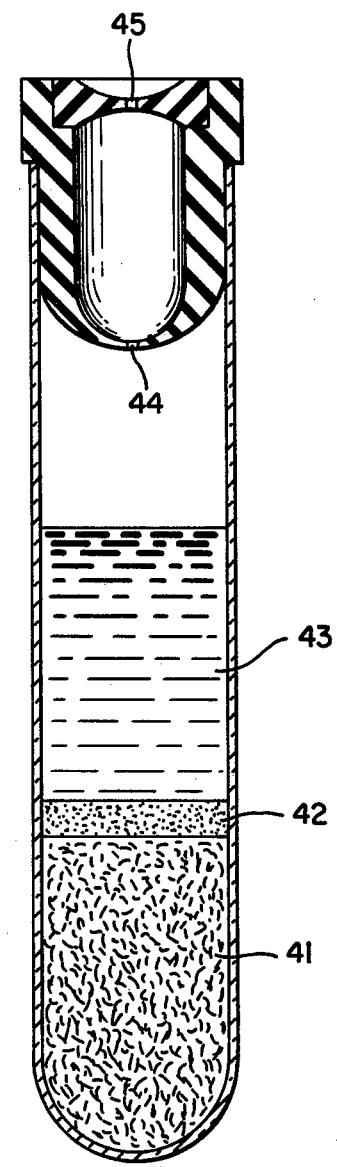
FIG. 4 is a longitudinal cross-sectional view of the embodiment of FIG. 3 following the separation and isolation of the serum or plasma from the blood.

The assembly of FIGS. 3 and 4 thus serve to collect and enclose blood without exposing the blood or the thixotrope to airborne contaminants.

Following the collection of the blood as shown in FIG. 3, the assembly is allowed to stand in order for clot formation to be complete. Following clot formation, the assembly as shown in FIG. 3 is centrifuged to affect a separation of blood serum 43 from the substantially cellular clot portion 41.

Upon centrifugation, passageway 44 will open outwardly due to the pressure being exerted on it by the relatively heavy thixotrope contained in reservoir 21. As the thixotrope is released from reservoir 21, the upper passageway 45 opens inwardly to allow air to enter and compensate for the reduced pressure formed within reservoir 21 by the removal of the thixotrope.

As the blood 32 is separated into clot portion 41 and serum portion 43 by centrifugation, the thixotrope is forced by centrifical force through passageway 45 and into blood 32. Having a specific gravity which is between that of serum 43 and cellular portion 41, the thixotrope establishes itself as a sealant barrier 42 at the interface between the serum 43 and clot 41 portions to form a relatively rigid barrier.

Following separation and isolation as described above, closure 10 may be removed and discarded to gain access to the serum 43, or the serum may be withdrawn by use of a cannula extending through closure 10.

Figure 2:
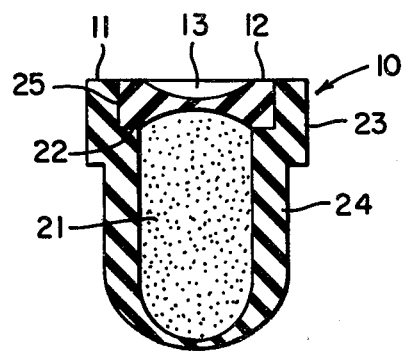
FIG. 2 is a longitudinal cross-sectional view of the enclosure of FIG. 1.
Figure 5:
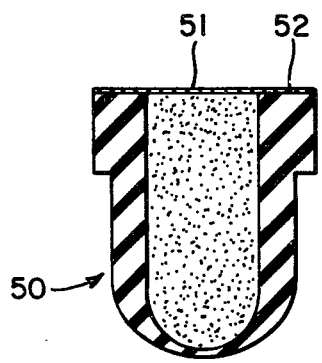
FIG. 5 is a longitudinal cross-sectional view of a further embodiment of the enclosure according to this invention.

A further embodiment of the closure is shown in FIG. 5. In this embodiment, the closure 50 is sealed about its upper circumferential surface 52 by a cannula penetrable membrane 51 in lieu of the seal 12 of FIG. 2. The use of the membrane 51, which may be of conventional sealing film material, obviates the need of a shaft 25 and shoulder 22 as seen in FIG. 2.

Having thus disclosed my invention, I claim:

1. An assembly for the collection, separation, isolation and storage of serum from blood which comprises:
   a tubular blood collection container (33) having an open end and a closed end;
   an elastomeric self-sealing cannula penetrable closure member (10) sealing said open end of the container, said closure member comprising:
   a hollow cylindrical body (24) extending into the open end of said container and being surmounted by a coaxial head (23) having a greater diameter than said body, said said head having a flange member (34) seated over the open end of the blood collection container;

an axially extending hollow shaft extending from said head through said body to a point just short of the lower terminus of said body, said lower terminus being of reduced thickness than the remainder of said body and forming a thin cannula penetrable zone;

an elastomeric self-sealing member (12) hermetically closing said hollow shaft at its upper most terminus;

said closed hollow shaft defining a reservoir (21) containing a thixotropic barrier material; and wherein said assembly is at least partially air evacuated.

2. An elastomeric self-sealing closure comprising a hollow cylindrical body surmounted by a coaxial head portion having a greater diameter than said body, a hollow central shaft extending axially through said body from said head portion to a point just short of the lower terminus of said body wherein the thickness of said body between said lower terminus and the hollow central shaft is less than the thickness between said shaft and the outer surface of said body, whereby there is formed a cannula penetrable bottom portion; a cannula penetrable seal positioned over the opened end of said hollow shaft in said head portion and sealing said hollow shaft, said sealed hollow shaft defining a reservoir; and said reservoir containing a sterile thixotropic sealant barrier material.

* * * * *